(12) United States Patent
Chang et al.

(10) Patent No.: US 11,191,718 B2
(45) Date of Patent: Dec. 7, 2021

(54) OPHTHALMIC GEL AND PREPARATION METHOD THEREOF

(71) Applicant: Institute of Nuclear Energy Research, Atomic Energy Council, Executive Yuan, R.O.C., Taoyuan (TW)

(72) Inventors: Ming-Cheng Chang, Taoyuan (TW); Tsai-Yueh Luo, Taoyuan (TW); Cheng-Liang Peng, Taoyuan (TW); Kuan-Yin Chen, Taoyuan (TW)

(73) Assignee: INSTITUTE OF NUCLEAR ENERGY RESEARCH, ATOMIC ENERGY COUNCIL, EXECUTIVE YUAN, R.O.C, Taoyuan (TW)

(*) Notice: Subject to any disclaimer, the term of this patent is extended or adjusted under 35 U.S.C. 154(b) by 0 days.

(21) Appl. No.: 16/539,211

(22) Filed: Aug. 13, 2019

(65) Prior Publication Data
US 2020/0345631 A1 Nov. 5, 2020

(30) Foreign Application Priority Data
May 2, 2019 (TW) ................................ 108115254

(51) Int. Cl.
| | | |
|---|---|---|
| *A61K 9/00* | (2006.01) | |
| *A61K 9/06* | (2006.01) | |
| *A61K 9/127* | (2006.01) | |
| *A61K 9/107* | (2006.01) | |
| *A61K 31/165* | (2006.01) | |
| *A61K 47/36* | (2006.01) | |
| *A61K 47/42* | (2017.01) | |
| *A61K 47/12* | (2006.01) | |

(52) U.S. Cl.
CPC .............. *A61K 9/0048* (2013.01); *A61K 9/06* (2013.01); *A61K 9/1075* (2013.01); *A61K 9/127* (2013.01); *A61K 9/1277* (2013.01); *A61K 31/165* (2013.01); *A61K 47/12* (2013.01); *A61K 47/36* (2013.01); *A61K 47/42* (2013.01)

(58) Field of Classification Search
None
See application file for complete search history.

(56) References Cited

U.S. PATENT DOCUMENTS

| | | | |
|---|---|---|---|
| 9,265,782 B2* | 2/2016 | Robledo | ............ A61K 31/7048 |
| 2009/0169629 A1* | 7/2009 | Lambert | .............. A61K 31/216 |
| | | | 424/489 |
| 2020/0069696 A1* | 3/2020 | Liu | ........................ A61K 9/127 |

* cited by examiner

*Primary Examiner* — Lezah Roberts
(74) *Attorney, Agent, or Firm* — Locke Lord LLP; Tim Tingkang Xia, Esq.

(57) ABSTRACT

The present invention provides an ophthalmic gel and a preparation method thereof. The ophthalmic gel comprises: an antibiotic; a nanocarrier, wherein the nanocarrier is used to load the antibiotic; and a biodegradable matrix, wherein the biodegradable matrix is compatible with the nanocarrier to carry the nanocarrier. When the ophthalmic gel of the present invention is applied to the surface of the cornea and conjunctiva of the eyes, the biodegradable matrix is automatically degraded and the nanocarrier carried by the biodegradable matrix will slowly release the antibiotic, loaded in the nanocarrier, at an appropriate rate to overcome the high-frequency use of general ophthalmic drugs and easily caused blurred vision; the present invention further comprises an ophthalmic gel preparation method.

7 Claims, 10 Drawing Sheets

OPHTHALMIC GEL AND PREPARATION METHOD THEREOF

CROSS REFERENCE TO RELATED APPLICATION

This application also claims priority to Taiwan Patent Application No. 108115254 filed in the Taiwan Patent Office on May 2, 2019, the entire content of which is incorporated herein by reference.

BACKGROUND

Technical Field

The present invention relates to an ophthalmic gel, and more particularly to an ophthalmic gel comprising a nanocarrier.

Related Art

Since the eye is a closed organ with a slow blood circulation, most drugs cannot reach the eye at an effective dose when administered systemically. Therefore, in the part administered by the eye, the topical corneal dressing is usually used instead of the oral administration.

The topical corneal dressing technology for eye can be mainly divided into three types of drugs: eye drop, eye ointment and ophthalmic gel; the eye drop is a transparent liquid with high permeability, which enables the patient to quickly absorb drugs, however, due to the high permeability of eye drop, it is impossible to maintain the drug concentration for a long time at a certain dose, and a frequent use of eye drop is required to achieve an effective drug concentration; the eye ointment has a higher drug stability than the eye drop and can provide an effective concentration of the drug for a long time, but there are problems such as aganoblepharon, blurred vision due to low transparency, low patient's medication compliance and others; and, in addition, although the ophthalmic gel can prolong the release of the drug and overcome the problem of aganoblepharon, currently commercially available ophthalmic gels do not have the development of fat-soluble drugs dissolved in ophthalmic gels.

Furthermore, in the development of long-acting sustained-release drug therapy, it is currently possible to achieve sustained-release drugs through the use of liposome transport technology; the liposome is a bilayered fat globule formed by hydration of phospholipids. Its special bilayer membrane structure and controllable particle size can be used to load hydrophilic or hydrophobic drugs and serve as a drug carrier for targeted administration.

The features of liposome as a drug delivery system can be summarized as follows: 1. It has the characteristics of loading hydrophilic and hydrophobic drugs. In addition, since the outer layer of the liposome is hydrophilic, the water solubility of the hydrophobic drug can also be increased. 2. The liposome has a similar lipid structure to the cell membrane, and thus has biocompatible and biodegradable properties, and is a low toxicity carrier. 3. It can protect the drug from being decomposed by the metabolic system after the drug is introduced into the body, improve the availability of the drug, and reduce the damage of highly toxic drugs to tissues and organs, for example, amphotericin B has kidney toxicity, doxorubicin causes cardiotoxicity, and cisplatin and vincristine would affect the peripheral nerves. 4. The drug is loaded between the liposomes to achieve the effect of sustained release control. It can change the pharmacokinetics, increase the blood concentration, and change the distribution of the drug in the body tissue (biodistribution) by means of the various carrier compositions and particle sizes of the liposome.

However, although the liposome has the effect of slowing drug release, it is necessary to deliver the liposomes with the ocular epidemic drug to the ocular tissues through other carriers, for example, the therapeutic drug is delivered to the posterior part of the eye (such as the retina and choroid) by intravitreal injection. The use of such invasive methods for drug administration would cause psychological or physical inconvenience to patients and is relatively high in cost.

In view of this, there is a need to provide a new type of ophthalmic gel to solve the above problems.

SUMMARY

The problem to be solved by the present invention is to provide an ophthalmic gel, and in particular an ophthalmic gel comprising a nanocarrier.

To achieve the above object, the present invention discloses an ophthalmic gel, comprising: an antibiotic; a nanocarrier, wherein the nanocarrier is used to load the antibiotic; and a biodegradable matrix, wherein the biodegradable matrix is combined with the nanocarrier to carry the nanocarrier.

The present invention further discloses a preparation method of a hydrophilic antibiotic ophthalmic gel, which comprises the following steps:

(a) dissolving an antibiotic, a cholesterol, and a DSPC in dichloromethane, and performing reduced pressure concentration to remove the dichloromethane so as to obtain a mixture;

(b) adding water to the mixture for hydration reaction for 20 to 40 minutes, shaking and mixing for at least 30 minutes, and then filtering with a filter;

(c) rinsing a filter membrane of the filter with a buffer solution to obtain a plurality of liposomes;

(d) mixing a collagen, a gelatin and an sodium alginate in a ratio to form a biodegradable matrix mixture, wherein the ratio is 1% sodium alginate, 4% gelatin and 1 mg/ml collagen;

(e) mixing the liposomes in step (c) and the biodegradable matrix mixture in step (d), and allowing to stand at room temperature to be solidified; and (f) rinsing with 3% calcium chloride to obtain the ophthalmic gel.

The present invention further discloses a preparation method of a lipophilic antibiotic ophthalmic gel, comprising the following steps: step 1: preparing a lipophilic antibiotic micelle: adding 10 mg to 50 mg of lipophilic drug at ratio of (1:40) to (1:50) to an emulsifier which is cremophor-Rh4 to form a micelle, then adding acetone to completely dissolve the micelle, then allowing to stand for 24 hours to obtain a micelle film containing the lipophilic drug, then placing the micelle film into a centrifuge tube, and adding a buffer solution to completely soak the micelle film containing the lipophilic drug in the buffer solution; step 2: preparing the biodegradable matrix: sterilizing a collagen, a gelatin and an sodium alginate, then mixing the collagen, the gelatin and the sodium alginate at a ratio at 50° C. to form a biodegradable matrix, and finally allowing the biodegradable matrix to stand at room temperature for 2-3 hours to solidify the biodegradable matrix, wherein the ratio is 1% sodium alginate, 4% gelatin and 1 mg/ml collagen; and step 3: taking the lipophilic antibiotic micelles prepared in step 1 and the biodegradable matrix prepared in step 2, mixing them at 50° C., then allowing the mixed lipophilic antibiotic micelles and biodegradable matrix to stand at room temperature for 2 to 3 hours to be solidified, and rinsing with 3% calcium chloride ($CaCl_2$) to obtain the lipophilic antibiotic ophthalmic gel.

The efficacy of the present invention is mainly embodied in that: 1, the present invention utilizes a decomposable biomedical material to carry a nanocarrier (liposome or micelle) for increasing the time when a drug release carrier such as a liposome and a micelle nanocarrier remains in the affected part of the eye; 2, the present invention can effectively overcome the high-frequency use of general ophthalmic drugs and caused blurred vision; and 3, the present invention can provide a corneal dressing comprising a fat-soluble drug or a water-soluble drug.

DETAILED DESCRIPTION

The present invention is intended to provide a preferred embodiment or embodiment of the technical means for solving the problem, which is not intended to limit the scope of the practice of the present invention, that is, equivalent changes and modifications which are consistent with the scope of the patent application of the present invention, or made in accordance with the scope of the present invention, are covered by the present invention.

Figure 1:
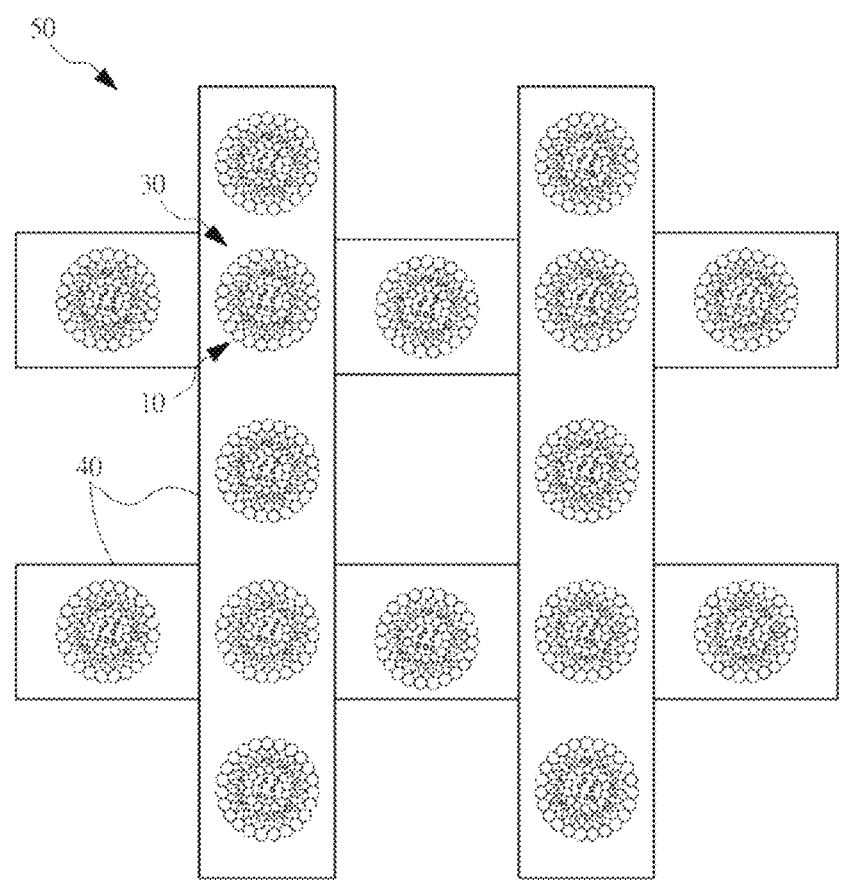
FIG. 1 is a schematic structural view of an ophthalmic gel according to the present invention.

Please refer to FIG. 1. FIG. 1 is a schematic structural view of an ophthalmic gel according to the present invention. The present invention provides an ophthalmic gel 50, comprising an antibiotic 10; a nanocarrier 30, wherein the nanocarrier 30 is used to load the antibiotic 10; and a biodegradable matrix 40, wherein the biodegradable matrix 40 is combined with the nanocarrier 30 to carry the nanocarrier 30. Features of the present invention are further described below.

Figure 2A:
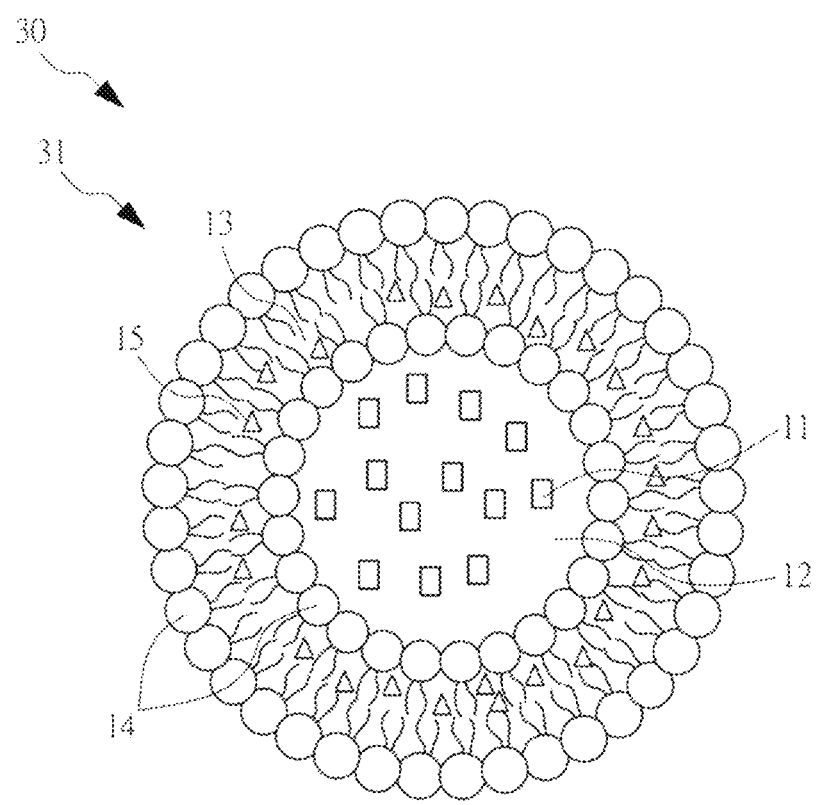
FIG. 2A and FIG. 2B are schematic structural views of a nanocarrier according to the present invention.
Figure 2B:
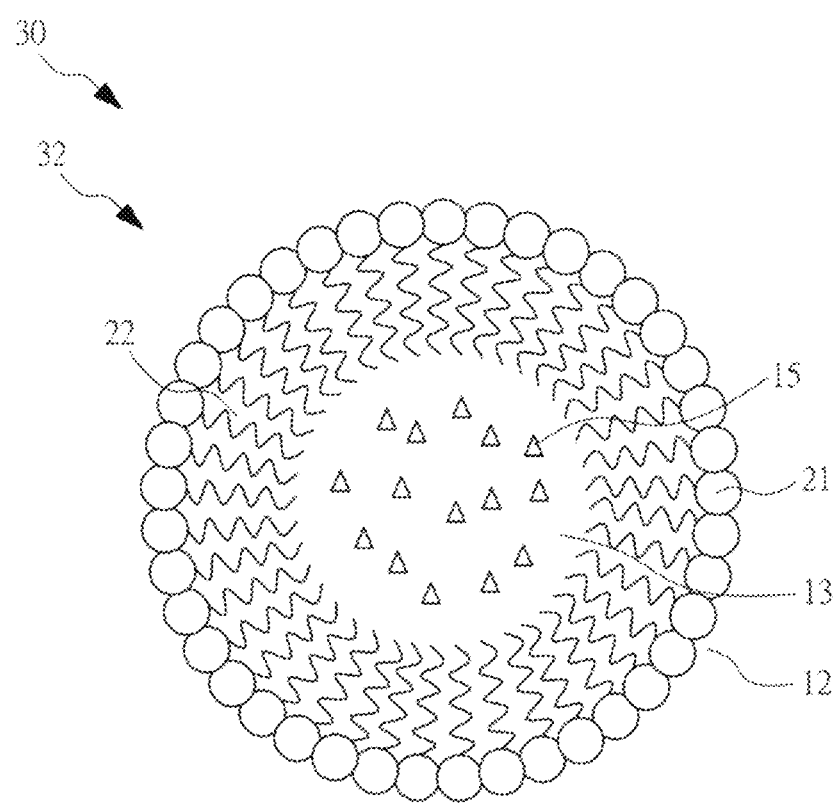

About the nanocarrier 30:

Please refer to FIG. 2A and FIG. 2B. FIG. 2A and FIG. 2B are schematic structural view of the nanocarrier according to the present invention. The nanocarrier 30 used in the ophthalmic gel 50 according to the present invention is a liposome 31 or a micelle 32. Among them, the liposome 31 is a pellet formed by dispersing a lipid or a phospholipid in a liquid phase, and is a concentric spherical structure formed by one or more layers of a phospholipid bilayer 14 separated by an aqueous phase. The phospholipid bilayer 14 forming the liposome is an amphiphile which is composed of a hydrophilic polar head group consisting of a phosphate group and two hydrophobic fatty acid chains. When the phospholipid molecules are dispersed in water, the hydrophilic head group is directed to the aqueous phase due to the difference in affinity and hydrophobicity at both ends, while the hydrophobic fatty acid chains tend to be closely arranged to each other, and self-assembled into a closed hollow sphere, that is, the liposome 31. Due to this special hollow sphere structure, the liposome 31 can serve as a carrier for a hydrophilic or hydrophobic drug at the same time; the hydrophilic drug 11 can be loaded in the central hydrophilic group 12, while the hydrophobic drug 15 can be loaded in the hydrophobic group interlayer 13 of the phospholipid bilayer 14.

Among them, the micelle 32 is the one whose molecules or ions will be self-assembled to form a nano-sized micelle after the surfactant (emulsifier) concentration in the solution reaches a certain critical value (i.e., the critical micelle concentration CMC) and exceeds this value.

Similar to liposome, it consists of a soluble and amphiphilic molecular chain with a hydrophilic chain 21 at one end and a hydrophobic chain 22 at the other end. When the amphoteric polymer is dissolved in an aqueous solution at a concentration exceeding the critical micelle concentration, the hydrophobic chains of the amphoteric polymer molecule would interact with each other through the Van Der Waals Force to combine and form a micelle structure with an internal hydrophobic group 13 and an external hydrophilic group 12, whose core structure may be the hydrophobic chain 22, and the outer layer is a hydrophilic chain 21 or an opposite structure. Among them, the hydrophobic drug 15 can be loaded in the hydrophobic group 13 of the micelle.

About antibiotic 10:

The antibiotic 10 used in the ophthalmic gel 50 according to the present invention can be classified into a water-soluble antibiotic and a fat-soluble antibiotic, wherein the water-soluble antibiotic is a hydrophilic drug 11, and the fat-soluble antibiotic is a hydrophobic drug 15.

About biodegradable matrix 40:

The biodegradable matrix 40 contained in the ophthalmic gel 50 according to the present invention is a high molecular polymer combined by collagen, gelatin and sodium alginate.

Collagen accounts for about 20% of total protein in mammals, and is an important protein in human connective tissue. It belongs to fibrin and is widely distributed in skin, joints, gums, etc. Meanwhile, collagen is also the main component of cornea in the eye.

Collagen is widely used as a biomedical material because it is derived from various connective tissues in animals and has good biocompatibility and biodegradability.

Gelatin, also known as fish gelatin or gelatine, is a light yellow transparent and tasteless gelatin made of animal skin and bone protein (i.e., collagen) and its main component is protein. Gelatin is commonly used as a gelling agent for foods, drugs or cosmetics. Gelatin is an irreversible hydrolyzed form of collagen and is classified as a food.

Alginic acid, also known as kelacid, alginate, and algin, is a natural polysaccharide found in the cell wall of brown algae. Usually the pure product is white to brownish yellow fiber, granule or powder. Alginic acid is easy to form a gel with a cation, such as sodium alginate, which is called seaweed gum, sodium alginate or phycocolloid.

Common brown algae such as kelp, sargassum, ascophyllum, and giant kelp are the main sources of alginic acid. The seaweed is treated with sodium hydroxide, and then the extract reacts with strong acid such as sulfuric acid to obtain alginic acid. *Azotobacter* and *Pseudomonas* can also be used for biosynthesis of alginic acid, and alginic acid synthesized by bacteria can usually produce micron- or nano-scale structures for biomedical engineering.

The biodegradable matrix as described herein is a main component in an ophthalmic gel, which can be combined with a nanocarrier and used to carry a nanocarrier loading an antibiotic (liposome or micelle). The principle of combining the biodegradable matrix with the nanocarrier is that the biodegradable matrix composed of collagen, gelatin and sodium alginate is a hydrophilic polymer with a network structure and thus can be compatible and combined with the hydrophilic polar head having a hydrophilic structure or hydrophilic chain of the aforementioned nanocarrier.

The ophthalmic gel according to the present invention is an ophthalmic gel comprising a nanocarrier, which is a new drug type "corneal dressing".

Figure 3:
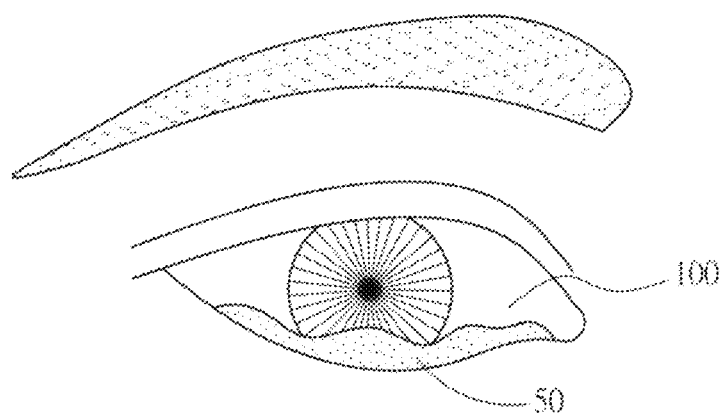
FIG. 3 is a schematic view showing the use of the ophthalmic gel according to the present invention.

Please refer to FIG. 3. FIG. 3 is a schematic view showing the use of the ophthalmic gel according to the present invention. When the ophthalmic gel 50 according to the present invention is applied to the corneal surface of the eye 100, the nanocarrier 30 (liposome 31 or micelle 32) covering antibiotic 10 is brought into the blood vessels of the eye tissue by the degradation of biodegradable matrix 40, so that the blood vessels of the eye tissue with poor blood circulation can effectively absorb the antibiotic drugs and the blood drug concentration surrounding the eye can be maintained at an effective drug concentration for a long time.

Furthermore, the transparency of the ophthalmic gel provided by the present invention can be further designed according to eye diseases and drug characteristics. For example, for a drug release carrier placed in a patient whose lower eyelid or cornea has been severely damaged, the transmittance can be temporarily ignored. The transparency of the ophthalmic gel provided by the present invention is mainly achieved by adjusting the ratio of the biodegradable matrix component.

Further, the present invention discloses various preparation methods for preparing the liposome or micelle containing antibiotics.

In accordance with an embodiment of the present invention regarding a method for preparing a liposome containing antibiotics, 1,2-distearoyl-3-sn-phosphatidylcholine (DSPC) and cholesterol at a certain molar ratio can be dissolved in dichloromethane (DCM), then the mixture is placed in a 50 mL round bottom flask and dried under reduced pressure at 60° C. using a rotary vacuum dryer until the DCM in the flask is completely drained, then 10 mg of antibiotics for hydration for 30 minutes is added, afterwards, the mixture is shaken by a probe-type ultrasound for 30 minutes, so that the lipid molecules are stripped from the wall of the flask and filtered through a 0.2 μm filter, the filter membrane is rinsed with 10 mL of buffer solution (pH=7.4). Finally, the hydrophilic drug not loaded with the liposome is removed by a PD-10 column, and the purified liposome is collected. For example, the molar ratio of 1,2-distearoyl-3-sn-phosphatidylcholine (DSPC) to cholesterol can be 6:1, 7:1, 8:1, or 9:1. In a specific embodiment, the molar ratio is 9:1.

In another embodiment for preparing an antibiotic liposome, 30 mg or 60 mg of antibiotic, 7.7 mg of cholesterol, and 110.6 mg of 1,2-distearoyl-3-sn-phosphatidylcholine (DSPC) drug are dissolved in dichloromethane (DCM), then the mixture is placed in a 50 mL round bottom flask and dried under reduced pressure at 60° C. using a rotary vacuum dryer until the DCM in the flask is completely drained, 10 mL of water for physiological test heated to 70° C. is added to carry out a hydration reaction for 30 minutes. Afterwards, the mixture is shaken by a probe-type ultrasound for 30 minutes. Then, the mixture is filtered through a 0.2 μm filter, and the filter membrane is rinsed with 10 mL of buffer solution. Finally, the active ingredient (e.g., antibiotic) not loaded with the liposome is removed by a PD-10 column, and the purified liposome is collected. In one embodiment, the molar ratio of the DSPC to cholesterol to antibiotic is 1:(5.5 to 9.5):(5 to 9). In a more specific embodiment, the molar ratio of DSPC to cholesterol to antibiotic is 1:(6.5 to 8.5):(6 to 8). In a more specific embodiment, the molar ratio of DSPC to cholesterol to antibiotic is 1:7.5:7.

In an embodiment of a micelle containing antibiotics, 10 mg of the lipophilic antibiotic is added to cremophor-Rh40 as emulsifier at a ratio of 1:50 for drug loading, then acetone is added to completely dissolve the micelle, and then the mixture is allowed to stand for 24 h and dry. Thereafter, the drug-containing micelle film is placed in a centrifuge tube, and PBS (pH=7.4) containing 0.5% tween-80 is added to completely soak the micelle film of the drug in the buffer solution.

The antibiotic may be a hydrophilic or lipophilic antibiotic. For example, the hydrophilic drug is selected from the group consisting of beta lactams (penicillin and its derivatives, cephalosporins, monobactams and carbapenems), glycopetides (vancomycin, teicoplanin, telavancin, bleomycin, ramoplanin and decaplanin) and aminoglycosides (amikacin, gentamicin, kanamycin, neomycin, netilmicin, paromomycin, streptomycin and tobramycin) and the like. The lipophilic drug is selected from the group consisting of macrolides (erythromycin, roxitromycin, clarithromycin, spiramycin, josamycin, and azithromycin), fluroquinolones (ciprofloxacin, levofloxacin, gatifloxacin, moxifloxacin, ofloxacin, and norfloxacin), tetracyclines (doxycycline, lymecycline, and minocycline), chloramphenicol, rifampin and the like.

Experimental Method

Transmission Electron Microscope Test

The liposomes or micelles are diluted 30 times and 100 times with the sterilized secondary water, respectively, then 7 μl of the diluted liposome or micelle sample is dropped on a copper mesh with a thickness of 5 to 6 nm and allowed to stand for one minute. The excess sample on the copper mesh is then absorbed with filter paper and 7 μl of 1-3% sodium (potassium) phosphotungstate (PTA) is added for counter-staining and allowed to stand for one minute. After that, the PTA on the copper mesh is absorbed by the filter paper, and then irradiated for 20 minutes under a heating lamp to dry the sample. The surface morphology of the liposomes or micelles can then be observed by a transmission electron microscope.

Particle Size Analysis of Nano-Liposomes

A particle size analyzer is used for analyzing the particle size of the liposomes or micelles. This instrument uses the principle of laser scattering to determine the particle size distribution of the liposomes or micelles. Under the irradiation of laser light, the scattered light reflected from the liposomes or micelles is detected by the instrument, and then converted into numerical data. After the obtained data is calculated by computer operation, the particle size distribution and average particle size of the liposomes or micelles can be known. The prepared liposomes or micelles are injected into a cuvette in an amount of about 1.5 ml, scanned under He—Ne laser at a wavelength of 636 nm, and analyzed by selecting particle size using a dynamic light scattering particle size interface potentiometer. The test is repeated for 3 times and the average value is taken. The scan range is from 3 to 3000 nm.

Loading Efficiency Detection 5 mL of the prepared liposome or micelle sample is taken, centrifuged by a centrifuge, and then the supernatant is introduced to the particle size analyzer for detection to determine that there is no liposome or micelle sample in the supernatant. The wavelength is set to 275 nm, and at least 20 µL of supernatant is drawn into the injection needle with a microinjection needle, and analyzed by HPLC. The drug loading efficiency is calculated as:

Drug loading efficiency (%)=weight of loaded drug/total weight of liposomes or micelles×100%. A fixed amount of liposomes or micelles is dissolved in ethanol/DMSO (1:2 v/v), and the absorption peak at a wavelength of 485 nm is measured. The weight of the loaded drug is calculated by comparing the calibration line of the drug in DMSO.

In Vitro Drug Release Assay 2 mL of the liposome or micelle solution containing the active ingredient (e.g., antibiotic) is placed in the dialysis membrane (isolated at a molecular weight of 3.5 kDa). The dialysis membrane is placed in an environment containing a 50 mL of normal saline (pH is about 7.4) at 37° C. for dialysis and the release drug is collected at regular intervals. The drug released is analyzed using a spectrophotometer at a wavelength of 274 nm. Upon carrying out the drug release analysis test of the antibiotic ophthalmic gel according to the present invention, the substance to be tested is placed in a dialysis membrane (isolated at a molecular weight of 3.5 kDa). The dialysis membrane is placed in an environment containing a 50 mL of normal saline (pH is about 7.4) at 37° C. for dialysis and the release drug is collected at regular intervals. The release drug is analyzed using a spectrophotometer at a wavelength of 274 nm.

Antibacterial Efficacy Analysis

The bacterial culture medium (LB) is inoculated with bacteria and culture is performed at 30° C. for 24 hours. A fixed amount of bacterial solution is introduced into the bacterial culture medium, and a fixed volume of the substance to be tested (e.g., antibiotic ophthalmic gel, etc.) is added. The control group uses sterile water instead of antibiotics and is cultured at 37° C., and samples are taken every other hour. Then, the absorbance is measured at a wavelength of 600 nm with a spectrophotometer to analyze the bacterial growth curve. After deducting the average absorbance of the blank group, the bacteria group without drugs is regarded as the survival rate of 100%. The absorbance of the bacteria group with drugs is divided by and the bacteria group without drugs to obtain the antibacterial rate at that time.

Cytotoxicity Test

Cell lines used for the toxicity test are human fibroblast HS-68 and epithelial cells, respectively. The cell culture medium is Dulbecco's modified eagle medium (DMEM) supplemented with 10% fetal bovine serum and 1% antibiotic, the cells are cultured and passaged at 37° C., 5% $CO_2$.

The prepared substance to be tested (e.g., antibiotic ophthalmic gel, etc.) is placed into a 6-well plate for cell culture, then 2×106 HS-68 cells or epithelial cells are added, and then placed in an incubator at 37° C., 5% $CO_2$ and cultured for 12 hours to allow the cells to be attached and restored healthy physiological activity. After 12 hours, the medium is sucked out and washed with PBS, and 0.5 mL of 0.05% Trypsin-EDTA solution is added, which is allowed to stand at 37° C. for several minutes and observed under an inverted microscope. When the cells are to be separated and presented in a round granular shape, the Trypsin-EDTA solution is removed by suction, and the edge of the culture plate is tapped gently to detach the cells. After that, 5 mL of cell culture medium is added and the cells are allowed to be evenly suspended in the culture medium. Then 100 µl of cell suspension is taken and mixed with 100 µl of 0.4% trypan blue in an equal volume evenly. A little mixed liquid (about 15 µl) is taken and added from the groove above the hemocytometer cell counting chamber, which is covered with a cover glass and observed under a 100-fold inverted microscope. The method for counting cells is to count the number of cells in each large square, multiply by the dilution factor and multiply by the constant 104, so as to obtain the quantity of cells per mL.

Statistical Analysis

Experimental data is analyzed by AVOVA or Student's t-test in SAS. The experimental data of the results is expressed by Mean±SEM, and p<0.05 means a significant difference.

EXAMPLES 1.1 Preparation of Chloramphenicol Liposome (LipoCAP)

Figure 6:
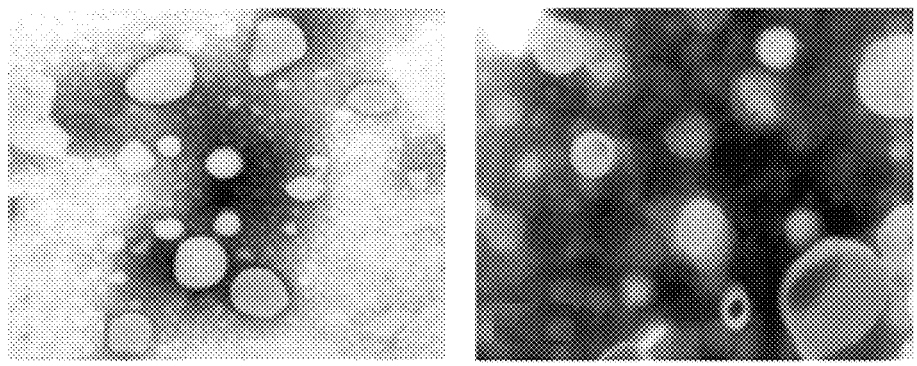
FIG. 6 is an image taken by a chloramphenicol liposome Lipo-CAP under a scanning electron microscope.

30 mg or 60 mg of chloramphenicol (CAP), 7.7 mg of cholesterol and 110.6 mg of 1,2-distearoyl-3-sn-phosphatidylcholine (DSPC) drug (molar ratio=14:15:2) are dissolved in dichloromethane (DCM) and then placed in a 50 mL round bottom flask. The mixture is dried under reduced pressure at 60° C. using a rotary vacuum dryer until the DCM in the flask is completely drained. 10 mL of water for physiological test heated to 70° C. is added to carry out a hydration reaction for 30 minutes. Afterwards, the mixture is shaken by a probe-type ultrasound for 30 minutes and filtered with a 0.2 µm filter, and the filter membrane is rinsed with 10 mL of buffer solution. The active ingredient not loaded with liposome (e.g., chloramphenicol) is removed by a PD-10 column and the purified chloramphenicol liposome (LipoCAP) is collected. The chloramphenicol liposome (LipoCAP) prepared in this Example is examined by the above-mentioned transmission electron microscopy test, and the photograph under the electron microscope is shown in FIG. 6. The photograph shows the single/double layered vesicle shape and hollow structure of the chloramphenicol liposome (LipoCAP). The size of the vesicles is about 200 nm, and the results show that the LipoCAP colloid had a hollow structure in its three-dimensional structure.

1.2 Preparation of Chloramphenicol Liposome (LipoCAP-S)

30 mg or 60 mg of chloramphenicol (CAP), 7.7 mg of cholesterol and 110.6 mg of 1,2-distearoyl-3-sn-phosphatidylcholine (DSPC) drug (molar ratio=14:15:2) are dissolved in dichloromethane (DCM) and then placed in a 50 mL round bottom flask. The mixture is dried under reduced pressure at 60° C. using a rotary vacuum dryer until the DCM in the flask is completely drained. 10 mL of water for physiological test heated to 70° C. is added to carry out a hydration reaction for 30 minutes. Afterwards, the mixture is shaken by a probe-type ultrasound for 30 minutes and filtered with a 0.2 μm filter. The filter membrane is rinsed with 10 mL of buffer solution, and the first 5 mL of drainage fluid (containing liposomes with a particle size of less than 200 nm) is collected. The active ingredient not loaded with liposome (e.g., chloramphenicol) is removed by a PD-10 column and the purified chloramphenicol liposome (LipoCAP-S) is collected.

1.3 Preparation of Biodegradable Matrix

A stock solution is prepared by sterilized collagen, gelatin and sodium alginate. The concentration of each component in the biodegradable matrix is 1% sodium alginate, 4% gelatin and 1 mg/ml collagen. The components are uniformly mixed at 50° C., and then placed at room temperature to stand for 2 hours to solidify the biodegradable matrix. Finally, the solidified biodegradable matrix is rinsed with 3% $CaCl_2$ to stabilize the structure and the biodegradable matrix is obtained.

1.4 Preparation of Ophthalmic Gel

A stock solution is prepared by sterilized collagen, gelatin and sodium alginate. The concentration of each component in the biodegradable matrix is 1% sodium alginate, 4% gelatin, and 1 mg/ml collagen. 300 μl of chloramphenicol liposomes prepared in Example 1.1 or 1.2 and 300 μl of biodegradable matrix (in a volume ratio of about 1:1) are uniformly mixed at 50° C., and then placed at room temperature to stand for 2 hours to solidify the biodegradable matrix. Finally, the solidified biodegradable matrix is rinsed with 3% $CaCl_2$ to stabilize the structure and the ophthalmic gel is obtained.

1.5 Preparation of 8-Hour Ophthalmic Gel Sustained Release Dosage Form

A stock solution is prepared by sterilized collagen, gelatin and sodium alginate. The concentration of each component in the biodegradable matrix is 1% sodium alginate, 4% gelatin, 0.01% sodium citrate and 1 mg/ml collagen. 300 μl of chloramphenicol liposomes prepared in Example 1.1 or 1.2 and 300 μl of biodegradable matrix (in a volume ratio of about 1:1) are uniformly mixed at 50° C., and then placed at room temperature to stand for 2 hours to solidify the biodegradable matrix. Finally, the solidified biodegradable matrix is rinsed with 3% $CaCl_2$ to stabilize the structure, and the 8-hour ophthalmic gel sustained release dosage form (CAG-LipoCAP-8) is obtained.

Example 2 Analysis of the Physical Properties of LipoCAP in Example 1.1

The particle size analysis of LipoCAP nano-liposomes of Example 1.1 is carried out by the above experimental method, and the results show that the chloramphenicol liposomes prepared by loading 30 mg of chloramphenicol with a liposome had an average particle size of 211.00+ 10.04 nm, chloramphenicol liposomes prepared with 60 mg of excess chloramphenicol had an average particle size of 305.57+19.83 nm.

Example 3 Analysis of Physical Properties of Biodegradable Matrix

The decomposition rate of the biodegradable matrix (final concentration: 1% sodium alginate, 4% gelatin and 1 mg/ml collagen) prepared in Example 1.3 is analyzed. In this example, different concentrations of sodium citrate are added to accelerate the decomposition of the biodegradable matrix. The concentration of sodium citrate is based on the permissible dose (less than 0.3%) of the commercially available eye lotion (normal saline).

Figure 5A:
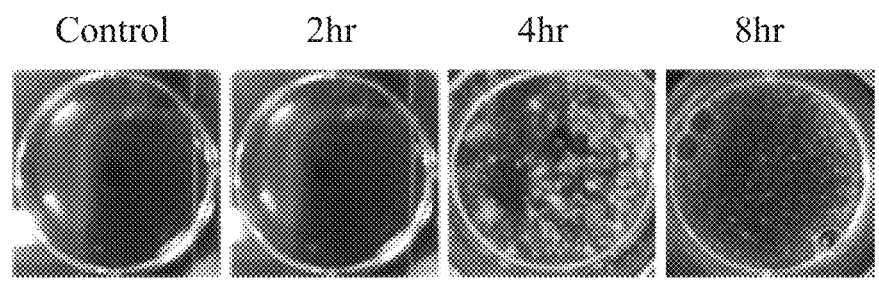
FIG. 5A is an image showing the decomposition state of a biodegradable matrix according to the present invention.
Figure 5B:
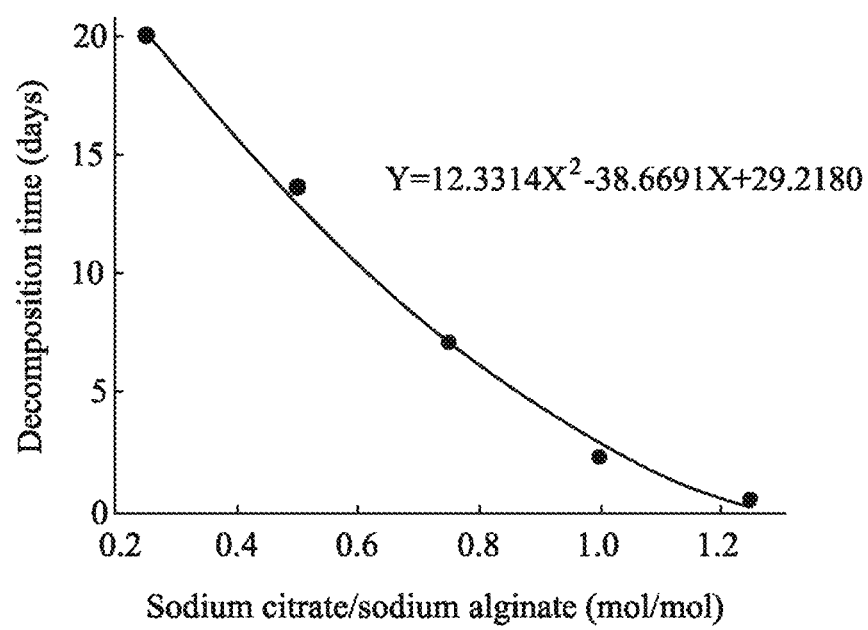
FIG. 5B is a relationship graph showing the molar ratio of sodium citrate to sodium alginate in a biodegradable matrix.

The results are shown in FIG. 5A and FIG. 5B. When the molar ratio of sodium citrate to sodium alginate is 1:0.25, the decomposition time of the biodegradable matrix is more than 20 days. As the molar ratio of sodium citrate to sodium alginate is increased, the decomposition time of the biodegradable matrix is significantly reduced. When the molar ratio of sodium citrate to sodium alginate is 1:1.25, the decomposition time of the biodegradable matrix is reduced to 11.51 hours (0.47 days) (the decomposition time of the biodegradable matrix is 13.61 days when the molar ratio is 1:0.5; the decomposition time of the biodegradable matrix is 7.15 days when the molar ratio is 1:0.75; the decomposition time of the biodegradable matrix is 2.24 days when the molar ratio is 1:1). By observing this phenomenon, the relationship curve of the decomposition time of the biodegradable matrix and the molar ratio of sodium citrate to sodium alginate is further established, where $Y=12.3314X^2-38.6691X+29.2180$ (Y is the decomposition time of the biodegradable matrix, and X is the molar ratio of sodium citrate to sodium alginate) (FIG. 5B). Thus, in accordance with an embodiment of the present invention regarding the 8 hour decomposable biodegradable matrix composite, the concentration of sodium citrate is determined as about 0.01% from the relationship curve provided by the equation.

The results of this study show that a short, median and long-acting decomposable biodegradable matrix bio-substrate for different applications can be established by adjusting the molar ratio of sodium citrate to sodium alginate according to this equation.

Example 4 Drug Release Concentration Test of LipoCAP Shown in Example 1.1.

Figure 4:
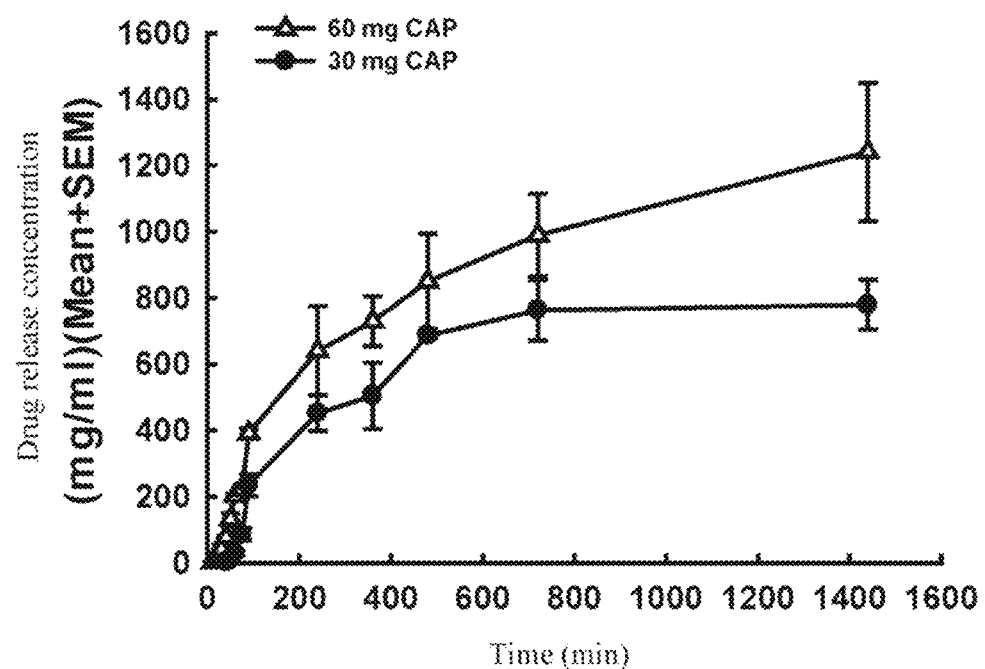
FIG. 4 is a graph showing the test of drug concentration of 60 mg of chloramphenicol liposome Lipo-CAP (represented by 60 mg of CAP in the figure) and 30 mg of chloramphenicol liposome Lipo-CAP (represented by 30 mg of CAP in the figure) according to the present invention.

The drug release rates of 30 mg of LipoCAP (30 mg of chloramphenicol) and 60 mg of LipoCAP (60 mg of chloramphenicol) are determined by the procedure shown in the above experimental method. The results are shown in FIG. 4. For the drug release of 30 mg of LipoCAP (30 mg of chloramphenicol) (shown as 30 mg CAP in FIG. 4), the effective drug dose is reached after 6 hours. In the drug release data of 60 mg of LipoCAP (60 mg of chloramphenicol) (shown as 60 mg CAP in FIG. 4), the effective drug dose (0.5 mg/mL) is reached after 4 hours. As a result of the test, it is found that the liposome proposed by the present invention has the effect of slowly releasing drugs.

Example 5 Drug Release Concentration Test of Ophthalmic Gel in Example 1.4 and 1.5

Figure 7:
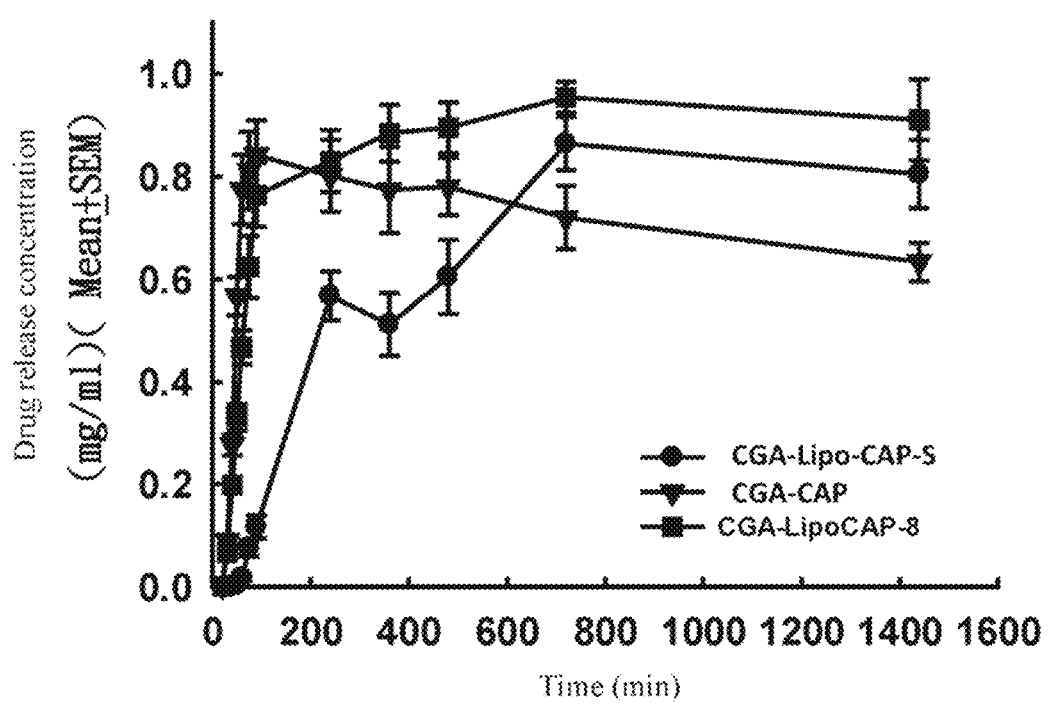
FIG. 7 is a graph showing the drug release concentration of an ophthalmic gel containing the chloramphenicol liposome according to an embodiment of the present invention.

The drug release concentrations of the ophthalmic gel in Examples 1.4 and 1.5 are determined by the procedure shown in the above experimental method. In this example, an ophthalmic gel containing 60 mg of LipoCAP-S is prepared from 60 mg of LipoCAP-S according to the procedure of Example 1.4, and an ophthalmic gel containing 60 mg of LipoCAP-8 is prepared from 60 mg of LipoCAP according to the procedure of Example 1.5. The results are shown in FIG. 7. The control group comprises an ophthalmic gel containing 60 mg of chloramphenicol, in which, although the control group can quickly reach the effective concentration of drug release, the drug release is stopped after 90 minutes. On the other hand, although the ophthalmic gel containing 60 mg of LipoCAP-S can continue the release of the drug, the initial drug release needs up to 4 hours to reach the effective drug dose. The ophthalmic gel containing 60 mg of LipoCAP-8 can achieve a pharmaceutically effective concentration after 75 minutes and the drug release time can last for up to 12 hours. The results show that the ophthalmic gel containing 60 mg of LipoCAP-8 has the advantages of simple drug loading and sustained release of drugs, and can quickly reach the pharmaceutically effective concentration and can continuously release the drug.

Example 6 Analysis of the Antibacterial Efficiency of Ophthalmic Gel in Examples 1.4 and 1.5

Figure 8:
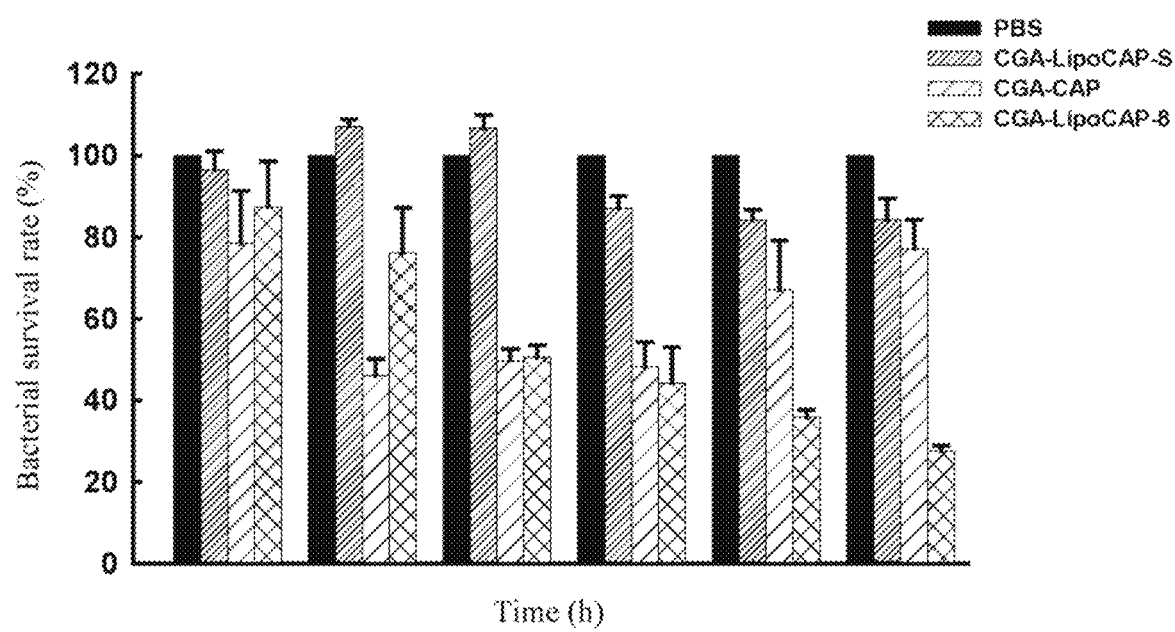
FIG. 8 is a bar graph showing the bacteriostatic ability of an ophthalmic gel containing the chloramphenicol liposome according to an embodiment of the present invention.

The ophthalmic gel drug (ophthalmic gel containing 60 mg of LipoCAP-S (shown as CGA-LipoCAP-S in the figure), ophthalmic gel containing 60 mg of LipoCAP-8 (shown as CGA-LipoCAP-8 in the figure) and control group ophthalmic gel containing 60 mg of chloramphenicol (shown as CGA-CAP in the figure) prepared according to various embodiments of the present invention is measured by the procedure shown in the above experimental method. The antibacterial effect of each ophthalmic gel is measured by using *Escherichia coli* as a research model in the example. The result is shown in FIG. 8. The *E. coli* concentration at each time point is used as a reference (100%), and the control group reaches the most obvious antibacterial amount at 4 hours, which is maintained for 8 hours. After 8 hours, since the drug concentration is no longer released, *E. coli* that is not inhibited and removed begins to proliferate again. In the analysis of the antibacterial ability of the ophthalmic gel group containing 60 mg of LipoCAP-S, since the drug cannot reach the effective concentration within a short time, a significant effect of inhibiting the growth of *E. coli* is not shown. The ophthalmic gel containing 60 mg of LipoCAP-8 can stabilize and continuously inhibit the proliferation of *E. coli*, and the phenomenon of inhibiting the proliferation of *E. coli* is more pronounced with the prolongation of time. The results show that the ophthalmic gel containing 60 mg of LipoCAP-8 can continuously release the drug, and even over 8 hours, the *E. coli* proliferation can be inhibited continuously with significant differences.

Example 7 Biocompatibility Analysis of Ophthalmic Gel in Examples 1.4 and 1.5

Figure 9:
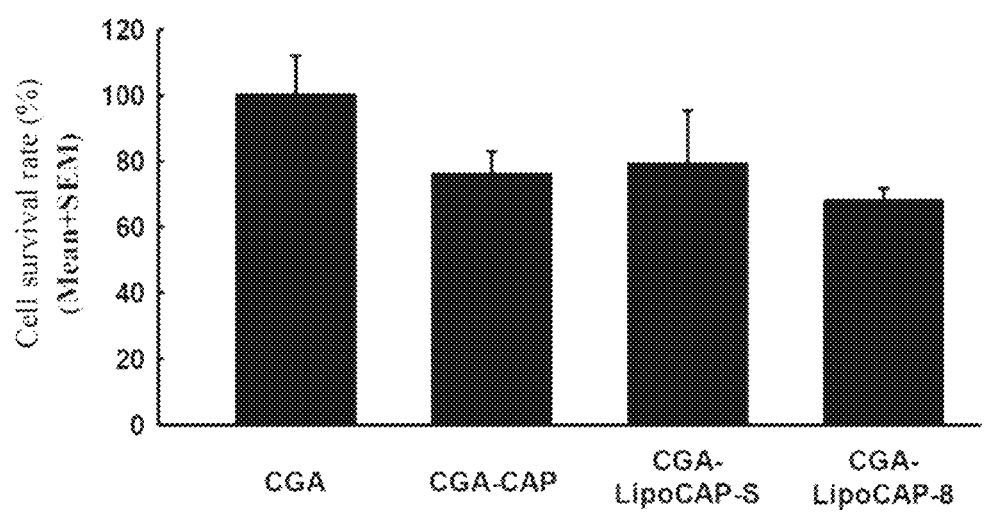
FIG. 9 is a graph showing the results of biocompatibility analysis of an ophthalmic gel according to another embodiment of the present invention.

In this example, whether the ophthalmic gel according to the present invention is toxic to normal cells, especially ocular epithelial cells, is analyzed. The biodegradable matrix of Example 1.3, the aforementioned ophthalmic gel containing chloramphenicol, ophthalmic gel containing LipoCap-S, and ophthalmic gel containing LipoCAP-8 are separately cultured for 12 hours with ocular epithelial cells. Cell counting is performed afterwards. In the case of 12 hours, the average cell survival rate after co-culture of the ocular epithelial cells with the biodegradable matrix in Example 1.3 (shown as CGA in the figure) is defined as 100% (FIG. 9). After co-culture of chloramphenicol ophthalmic gel (shown as CGA-CAP in the figure), ophthalmic gel containing LipoCap-S (shown as CGA-LipoCap-S in the figure) and ophthalmic gel containing LipoCAP-8 (shown as CGA-LipoCAP-8 in the figure), the cell survival rates are 76.01+6.87%, 79.17+16.16% and 67.87+3.7587%, respectively, and there is no significant difference between the three. The results of this study show that new formulations of sustained release drugs such as CGA-CAP, CGA-LipoCap-S and CGA-LipoCAP-8 are not significantly toxic to ocular epithelial cells.

What is claimed is:

1. An ophthalmic gel, comprising:
   an antibiotic;
   a nanocarrier, loading the antibiotic, wherein the nanocarrier is a liposome and consists of cholesterol and 1,2-distearoyl-3-sn-phosphatidylcholine (DSPC), and wherein the molar ratio of DSPC to cholesterol to antibiotic is 1:(5.5 to 9.5):(5 to 9); and
   a biodegradable matrix, wherein the biodegradable matrix is combined with the nanocarrier to carry the nanocarrier, wherein the biodegradable matrix consists of collagen, gelatin, sodium alginate and sodium citrate, and the molar ratio of the sodium citrate to the sodium alginate is (1:0.1) to (1:2), and the biodegradable matrix comprises 1% sodium alginate, 4% gelatin and 1 mg/ml collagen.

2. The ophthalmic gel according to claim 1, wherein the molar ratio of DSPC to cholesterol to antibiotic is 1:7.5:7.

3. The ophthalmic gel according to claim 1, wherein the antibiotic is selected from the group consisting of penicillin derivatives, cephalosporins, monobactams, carbapenems, vancomycin, teicoplanin, telavancin, bleomycin, ramoplanin, decaplanin, amikacin, gentamicin, kanamycin, neomycin, netilmicin, paromomycin, streptomycin, tobramycin, moxifoxacin, erythromycin, roxitromycin, clarithromycin, spiramycin, josamycin, azithromycin, ciprofloxacin, levofloxacin, gatifloxacin, moxifloxacin, ofloxacin, norfloxacin, doxycycline, lymecycline, minocycline, chloramphenicol, and rifampin.

4. A method for preparing the ophthalmic gel according to claim 1, comprising the following steps:
   (a) dissolving an antibiotic, a cholesterol, and a DSPC in dichloromethane, and performing reduced pressure concentration to remove the dichloromethane so as to obtain a mixture;
   (b) adding water to the mixture for hydration reaction for 20 to 40 minutes, shaking and mixing for at least 30 minutes, and then filtering with a filter;
   (c) rinsing a filter membrane of the filter with a buffer solution to obtain a plurality of liposomes;
   (d) mixing a collagen, a gelatin and an sodium alginate in a ratio to form a biodegradable matrix mixture, wherein the ratio is 1% sodium alginate, 4% gelatin and 1 mg/ml collagen;
   (e) mixing the liposomes in step (c) and the biodegradable matrix mixture in step (d), and allowing to stand at room temperature to be solidified; and
   (f) rinsing with 3% calcium chloride to obtain the ophthalmic gel.

5. The method according to claim 4, wherein the molar ratio of DSPC to cholesterol to antibiotic is 1:(5.5 to 9.5):(5 to 9).

6. The method according to claim 5, wherein the molar ratio of DSPC to cholesterol to antibiotic is 1:7.5:7.

7. The method according to claim 6, wherein the antibiotic is selected from the group consisting of penicillin, cephalosporins, monobactams, carbapenems, vancomycin, teicoplanin, telavancin, bleomycin, ramoplanin, decaplanin, amikacin, gentamicin, kanamycin, neomycin, netilmicin, paromomycin, streptomycin, tobramycin, moxifoxacin, erythromycin, roxitromycin, clarithromycin, spiramycin, josamycin, azithromycin, ciprofloxacin, levofloxacin, gatifloxacin, moxifloxacin, ofloxacin, norfloxacin, doxycycline, lymecycline, minocycline, chloramphenicol, and rifampin.

\* \* \* \* \*